United States Patent [19]
Jendryssek-Pfaff et al.

[11] Patent Number: 5,538,720
[45] Date of Patent: Jul. 23, 1996

[54] HAIR TREATMENT COMPOSITION AND PROCESS USING METAL SALTS

[75] Inventors: Madeleine Jendryssek-Pfaff, Aschach; Satoshi Onitsuka, Darmstadt, both of Germany

[73] Assignee: Kao Corporation, Tokyo, Japan

[21] Appl. No.: 106,997

[22] Filed: Aug. 17, 1993

[30] Foreign Application Priority Data

Aug. 17, 1992 [DE] Germany .................. 42 27 203.3

[51] Int. Cl.$^6$ .................................................. A61K 7/075
[52] U.S. Cl. .................. 424/70.1; 424/70.4; 424/70.13
[58] Field of Search ........................ 424/70, 71, 401, 424/70.4, 70.13, 70.21, 70.28

[56] References Cited

U.S. PATENT DOCUMENTS

| | | |
|---|---|---|
| 5,051,252 | 9/1991 | Schultz et al. .................. 424/71 |
| 5,104,646 | 4/1992 | Bolich, Jr. et al. .................. 424/70 |

OTHER PUBLICATIONS

Harry's Cosmeticology by Ralph G. Harry pp. 408–410 (1973).
CA: 48206n "Carrier gels for cosmetic and pharmaceuticals" (1975).

*Primary Examiner*—Jyothsna Venkat
*Attorney, Agent, or Firm*—Birch, Stewart, Kolasch & Birch

[57] ABSTRACT

A composition for hair treatment comprising at least two compositions (A) and (B) that are kept separate until application and that upon mixing increase in viscosity while generating heat, wherein one composition (A) comprises an essentially anhydrous mixture of a physiologically compatible salt that generates heat when mixed with water, and at least one thickening agent, and composition (B) comprising at least one polyalcohol that is liquid at 25° C. and is selected from the group consisting of polyethyleneglycol, polypropyleneglycol, glycerol and diglycerol and, optionally, additional hair conditioning. A process for hair treatment, wherein composition (B) is first mixed with water and then blended with composition (A), whereby, while generating heat, a viscous gel develops that is applied onto the hair where it provides an enhanced conditioning effect due to improved penetration at higher temperature.

10 Claims, No Drawings

HAIR TREATMENT COMPOSITION AND PROCESS USING METAL SALTS

This invention comprises a composition and a process for the treatment of hair providing an improved conditioning effect compared with conventional compositions.

BACKGROUND OF THE INVENTION

Hair conditioning compositions have been long known and are very popular among users, particularly female consumers. The hair conditioning compositions are usually applied after hair cleansing, dyeing or waving processes. Above all, the hair conditions compositions are used to restore hair structure, improve lustre and touch thereof, ease combability of wet and dry hair, and provide a lasting hair style.

The number of active substances suggested for this purpose is immense; reference is, e.g., made to the monography of K. Schrader, "Grundlagen und Rezepturen der Kosmetika", 2nd Edition (1989, Hüthig Buchverlag, Heidelberg), pp. 722 to 781.

Known hair conditioning compositions still require improvement, despite of the multitude of known and suggested formulations, especially with regard to their ability to penetrate into the hair.

SUMMARY OF THE INVENTION

It has now been found that an excellent conditioning effect can be achieved if the hair is treated with a composition obtained by admixture of two compositions kept separate until application, wherein one composition (A) is essentially anhydrous and contains a physiologically compatible salt that generates heat upon admixture with water, and at least one thickening agent, and a second composition (B) that contains at least one polyalcohol that is liquid at 25° C. and is selected from the group consisting of polyethyleneglycol, polypropyleneglycol, glycerol and diglycerol, whereby these compositions are, under the addition of water, mixed while heat is generated, and the warm gel thus obtained is applied onto human hair and rinsed after processing.

Without adhering any theory, it is believed that the heat treatment essentially increases the penetration of the active ingredients into the hair, wherein the active ingredients may either the salts that generate heat when mixed with water, especially if these salts are bivalent metal chlorides according to a preferred embodiment of the invention, such as calcium chloride, magnesium chloride or zinc chloride, or additionally used known hair conditioning substances.

As indicated above, the physiologically compatible salt that develops heat when mixed with water is preferably a bivalent metal chloride.

Such bivalent metal chlorides are in particular calcium chloride, magnesium chloride or zinc chloride, which also have an additional hair conditioning effect.

Other suitable salts are aluminum chloride, sodium sulfate, sodium carbonate, or beryllium chloride.

The quantity of the metal chloride required to develop heat depends on the desired temperature of the ready-to-use composition, wherein the desired temperature is about 40° to 60° C., and is preferably about 50° C.

The same applies for the thickening agent present in the anhydrous composition in admixture with the heat-developing salt, wherein the proportion of salt to thickening agent should generally be about 1:1 to 50:1, and particularly about 2 to 5:1.

Suitable thickening agents in particular are various cellulose derivatives such as methyl cellulose, hydroxyethyl cellulose, hydroxypropyl cellulose, or natural gums such as xanthan gum, guar gum/and pectin; in addition, inorganic thickening agents, e.g. aluminium silicate, and magnesium aluminium silicates such as montmorillonite or silica, may be used.

The essential component of composition (B), which is kept separate from the composition (A) containing the anhydrous salt, is a polyalcohol that is in a liquid state at 25° C., and is selected from the group of polyethyleneglycol, polypropyleneglycol, glycerol and diglycerol.

The preferred weight proportion of the heat-developing salt when mixed with water in relation to polyalcohol in the ready-to-use mixture is between about 1:1 and 1:8, and especially 1:2 and 1:6.

A polyethyleneglycol having a molecular weight from about 200 to 600, and especially from about 400 to about 600, is preferred as the polyalcohol.

The polyalcohol in the ready-to-use composition has a dual function: firstly it serves as a carrier, and secondly, it serves as a thermal reservoir to maintain the heat developed by the mixture of the metal salt with water for a reasonable time in the final viscous product.

This function is best fulfilled by polyethyleneglycol, particularly with a molecular weight between 200 and 600, since it generates additional heat; other suitable polyalcohols such as polypropyleneglycol and glycerol or diglycerol, which are preferably used in admixture with polyethyleneglycol, do not develop heat in combination with water, but are suitable to act as a thermal reservoir.

Higher oligoglycerols such as tri-, tetra- and pentaglycerols may be used in admixture with the polyalcohols mentioned above, provided that the mixture is liquid at a temperature of 25° C.

The compositions according to the invention may be applied onto the hair and have a conditioning effect as already described, when containing, in particular, bivalent metal chlorides such as calcium chloride, magnesium chloride and zinc chloride (wherein calcium chloride is preferred).

It is however expedient and advantageous to use additional hair conditioning substances known.

In particular known long-chain quaternary ammonium compounds or cationic polymers are mentioned as such.

Further film-forming agents such as ampholytic, agents such as nonionic and anionic polymers may be used for this purpose, as well as natural and synthetic fats and oils, volatile and non-volatile silicones, humectants, amino acids, panthenol, phytantriol, and naphthaline sulfonic acid.

Apart from active agents, auxiliaries may also be used, e.g., anionic, nonionic or amphoteric surfactants, preservatives.

The relevant performance of these compounds and their concentrations of use are known in the art, see, e.g., K. Schrader, l.c. and, for that reason a specific enumeration thereof is not necessary.

These additional hair conditioning compounds may be added to either composition (A) or composition (B); if they are present in liquid form or in solution or dispersion it is more suitable to add these additional hair conditioning compounds to, composition (B).

The composition according to the invention may be applied as follows:

A receptacle, e.g. a vial, comprising the polyalcoholic composition (B), preferably in combination with hair conditioning substances and optionally with surfactants (about 5 to 20 g), is filled with water (about 30 ml), and the solution thus obtained is added to the anhydrous composition (A) comprising an anhydrous salt that generates heat in combination with water and thickening agents (about 5 g in a proportion of about 9:1), and is mixed. A temperature from about 50° to 55° C. is generated while a gel composition is formed. This composition is applied onto wet hair and allowed to act for about 10 minutes, whereby the temperature slowly decreases to about 40° C. Thereafter the treated hair is rinsed.

The sequence of admixture of the compositions (A) and (B) may also be reversed.

Composition (B) comprising the polyalcohol may additionally contain a water-free alcohol, such as 1,3- or 1,4-butanediol, benzyl alcohol, benzyloxyethanol, 1-methoxypropanol, or dipropyleneglycol monomethylether to improve penetration.

The proportion of penetration promoter may be between 0 and 25% by weight of the composition (B).

A general formula of the compositions according to the invention is defined about as follows:

| | |
|---|---|
| Calcium chloride, magnesium chloride or zinc chloride | 1–70, preferably 1–25, most preferred 3–15% by wt.; |
| Polyethyleneglycol (MG 200–600) | 1–60, preferably 1–40, most preferred 5–30% by wt.; |
| Thickening agent | 0.5–15, preferably 1–10, most preferred 1.5–8% by wt; |
| Water | @ 100% by wt. |

These percentages refer to the ready-to-use mixture.

The metal salt proportions obviously depend on the fact whether or not they are free from crystal water which are preferred, or crystal water containing salts. In the first case the levels are lower, in the second case higher.

The following examples further illustrate the invention:

|  |  | Composition No. | | | | |
|---|---|---|---|---|---|---|
|  |  | 1 | 2 | 3 | 4 | 5 |
| Comp. A | Calcium chloride (anhydrous) | 10% | 6% | 15% | 8% | 8% |
|  | Hydroxymethyl cellulose | 2% | 2% | 3% |  | 2% |
|  | SiO$_2$ und Al$_2$O$_3$ |  |  |  | 4% |  |
| Comp. B | Polyethyleneglycol (MG: 200–600) | 25% | 30% | 35% | 20% | 16% |
|  | C$_{11-15}$-Pareth 9 | 1% | 1% | 2% |  |  |
|  | C$_{10}$–C$_{12}$-Alkyl glucoside (40–45%)(P.D:1.4) |  |  |  | 2% |  |
|  | Pentaerythrol isostearyl glyceryl ether | 1% | 2% | 1% |  |  |
|  | Glycerol |  | 2% | 2% |  |  |
|  | Keratin hydrolysate (30%) |  |  | 2% |  |  |
|  | Elastin hydrolysate (15%) |  |  |  | 3% | 3% |
|  | Silicone oil (Polydimethicone) | 2% |  |  | 1% |  |
|  | Steartrimonium chloride (40%) | 4% |  | 2% |  |  |
|  | Quaternium 80 (50%) |  | 4% |  |  |  |
|  | Polyquaternium 11 (50%) |  |  |  | 7% | 8% |
|  | Isopropyl palmitate |  | 2% | 3% |  |  |
|  | Cholesteryl isostearate | 2% |  |  |  |  |
|  | Jojoba oil |  |  |  |  | 0.4% |
|  | Ethyl carbitol |  |  |  |  | 8% |
|  | Allantoin/Acetylmethionine |  |  |  | 0.2% |  |
|  | Lactic acid |  |  | 0.4% | 0.4% |  |
| Water at application of the product |  | @100 | @100 | @100 | @100 | @100% |

Hair treated with these compositions is fuller in volume and has a firm hold, but a relaxed touch and natural gloss.

We claim:

1. A composition for the treatment of human hair, comprising compositions (A) and (B) that are kept separate until application and that, upon admixture in the presence of water, increase in viscosity while generating heat, wherein an essentially anhydrous composition (A) comprises a physiologically compatible salt selected from the group consisting of calcium chloride, magnesium chloride, zinc chloride, aluminum chloride, sodium sulfate, sodium carbonate and beryllium chloride and that generates heat when mixed with water, and one or more thickening agents selected from the group consisting of methyl cellulose, hydroxyethyl cellulose, hydroxypropyl cellulose, xanthan gum, guar gum, pectin, silica, magnesium aluminum silicate and aluminum silicate, and composition (B) comprises one or more polyalcohols that is liquid at 25° C. and, is selected from the group consisting of polyethyleneglycol, polypropyleneglycol, glycerol and diglycerol.

2. The composition according to claim 1, wherein said polyalcohol is a polyethyleneglycol having a molecular weight between 200 and 600.

3. The composition according to claim 2, wherein said polyethyleneglycol has a molecular weight from 400 to 600.

4. The composition according to claim 1, wherein the weight proportion of said physiologically compatible salt that generates heat when mixed with water to said liquid polyalcohol is between 1:1 and 1:8 in the final mixture to be applied onto the hair.

5. The composition according to claim 4, wherein the weight proportion of said physiologically compatible salt that generates heat when mixed with water to said liquid polyalcohol is between 1:2 to 1:6.

6. The composition according to claim 1, further comprising a film-forming agent.

7. The composition according to claim 1, further comprising a hair conditioning substance.

8. The composition according to claim 1, wherein composition (B) further comprises a penetration promoter.

9. The composition according to claim 8, wherein said penetration promoter is selected from the group consisting of 1,3-butanediol, 1,4-butanediol, benzyl alcohol and benyloxyethanol.

10. A process for the treatment of hair, comprising the steps of mixing an essentially anhydrous composition (A) comprising a physiologically compatible salt selected from the group consisting of calcium chloride, magnesium chloride, zinc chloride, aluminum chloride, sodium sulfate, sodium carbonate and beryllium chloride and that develops heat upon admixture with water and one or more thickening agents selected from the group consisting of methyl cellulose, hydroxyethyl cellulose, hydroxypropyl cellulose, xanthan gum, guar gum, pectin, silica, magnesium aluminum silicate and aluminum silicate, water, and a composition (B) comprising one or more polyalcohols that is liquid at 25° C. and is selected from the group consisting of polyethyleneglycol, polypropyleneglycol and di-, tri- or polyglycerol, wherein heat is generated while viscosity of the mixture increases during mixing to obtain a gel, applying said gel onto human hair, and rinsing said gel after processing.

* * * * *